US006423324B1

(12) United States Patent
Murphy et al.

(10) Patent No.: US 6,423,324 B1
(45) Date of Patent: Jul. 23, 2002

(54) TEMPERATURE-STABLE POLYAMIDE RESIN-BASED COMPOSITION, AND PRODUCTS

(75) Inventors: John Murphy, Fayetteville; John Cunningham, Franklin; Angie Sanders, Lewisburg, all of TN (US)

(73) Assignee: Cosmolab, Inc., Lewisburg, TN (US)

( * ) Notice: Subject to any disclaimer, the term of this patent is extended or adjusted under 35 U.S.C. 154(b) by 0 days.

(21) Appl. No.: 09/597,474

(22) Filed: Jun. 20, 2000

(51) Int. Cl.$^7$ .......................... A61K 7/02; A61K 7/025
(52) U.S. Cl. .................. 424/401; 424/64; 424/78.03
(58) Field of Search ................ 424/401, 64, 78.03

(56) References Cited

U.S. PATENT DOCUMENTS

| | | | |
|---|---|---|---|
| 3,148,125 A | 9/1964 | Strianse et al. | 167/85 |
| 3,819,342 A | 6/1974 | Gunderman et al. | 44/7.5 |
| 3,969,087 A | 7/1976 | Saito et al. | 44/7 |
| 5,429,816 A | 7/1995 | Hofrichter et al. | 424/66 |
| 5,500,209 A | 3/1996 | Ross et al. | 424/66 |
| 5,843,194 A | 12/1998 | Spaulding | 44/275 |
| 5,843,407 A | 12/1998 | El-Nokaly et al. | 424/64 |
| 5,976,514 A | 11/1999 | Guskey et al. | 424/65 |
| 5,998,570 A | 12/1999 | Pavlin et al. | 528/310 |

FOREIGN PATENT DOCUMENTS

| | | |
|---|---|---|
| EP | 0 797 976 A2 | 10/1997 |
| JP | 1207223 A | 8/1989 |
| JP | 2180805 A | 7/1990 |

OTHER PUBLICATIONS

International Search Report of PCT/US01/17643 dated Feb. 25, 2002.
Anjinomoto Co. Inc., Product Bulletin and Material Safety Data Sheet for Oil Gelatinication agent GP–1, Jan. 7, 1991.
Presperse Inc., Permethyl® Product Bulletin, Jun. 12, 1991, South Plainfield, New Jersey.
Amoco Chemical Company, Product Bulletin for Amoco® Polybutenes, 1992 (place of publication unknown).
Kirk–Othmer, *Encyclopedia of Chemical Technology*, vol. 8, 1993, pp. 91, 103, 129, 135, 232–236.
Henkel Corporation, Material Safety Data Sheet for VER-SAMID® 1655 Thermographic Resin, Feb. 1993, Ambler, Pennsylvania.
Henkel Corporation, Material Safety Data Sheet for VER-SAMID® 930 Co–Solvent Soluble Polyamide Resin, Feb. 1993, Ambler, Pennsylvania.
Henkel Corporation, Material Safety Data Sheet for VER-SAMID® 963 Co–Solvent Soluble Polyamide Resin, Feb. 1993, Ambler, Pennsylvania.
Henkel Corporation, Material Safety Data Sheet for VER-SAMID® 754 Alcohol Soluble Polyamide Resin, Mar. 1993, Ambler, Pennsylvania.
M.M.P., Inc., Material Safety Data Sheet for Octyl Dodecanol, Aug. 1993, Plainfield, New Jersey.
ICI Americas Inc., Product Bulletin—HLB Values of ICI Surfactants, 1995 (place of publication unknown).
Amoco Chemical Company, Material Safety Data Sheet for INDOPOL® H–100, Feb. 27, 1997, Chicago, Illinois.
LIPO Chemicals Inc., Material Safety Data Sheet for LIPOSORB O, Feb. 4, 1998, Paterson, New Jersey.
Research Solvents and Chemicals, Inc., Material Safety Data Sheet for for Isopropyl Alcohol, Mar. 17, 1998, Pelham, Alabama.
LIPO Chemicals Inc., Materials Safety Data Sheet for LIPOSORB O–20, Jul. 7, 1998, Paterson, New Jersey.
HANSOTECH Inc., Material Safety Data Sheet for Castor Oil Triglyceride of Ricinoleic Acid, Mar. 2000, Woodbury, New York.
BFGOODRICH Performance Materials, Material Safety Data Sheet for ULTRACAS G20, Mar. 6, 2000, Cleveland, Ohio.

*Primary Examiner*—Jose G. Dees
*Assistant Examiner*—Michael A. Williamson
(74) *Attorney, Agent, or Firm*—Marshall, Gerstein & Borun

(57) ABSTRACT

A temperature-stable cosmetic composition including a polyamide resin, a solvent for the polyamide resin, and a gelling agent selected from the group consisting of N-acyl amino acid amides, N-acyl amino acid esters, and mixtures thereof, is disclosed. A composition of the invention can be made translucent or transparent, need not require specialized packaging and containers, is not subject to hardening caused by evaporation of volatile alcohols, is temperature-stable over a period of several weeks, and exhibits excellent esthetic and functional properties, including sensory properties, for consumer acceptance.

15 Claims, No Drawings

TEMPERATURE-STABLE POLYAMIDE RESIN-BASED COMPOSITION, AND PRODUCTS

BACKGROUND OF THE INVENTION

1. Field of the Invention

The invention generally relates to temperature-stable polyamide resin-based compositions, and, more specifically, to translucent or transparent, temperature-stable, polyamide resin-based compounds for use in cosmetics, particularly in lipstick, lip gloss, and lip balm products.

2. Brief Description of Related Technology

The structure of conventional lipsticks is provided by a mixture of solid, semi-solid, and liquid lipids, such as waxes and emollients. Waxes are typically used to suspend or co-solubilize oils into a single-phase, solid structure. Conventional lipsticks are opaque.

In another type of lipstick composition, the structure is provided by a solid polyamide resin. Such a lipstick is disclosed in Strianse et al. U.S. Pat. No. 3,148,125 (Sep. 8, 1964), the disclosure of which is hereby incorporated herein by reference. The resin is a solid, but soluble, condensation product of an aliphatic dicarboxylic acid and a diamine. The polyamide resin is compounded with solvents, such as lower aliphatic alcohols and fatty acid esters, which act as softening agents. A lipstick containing a polyamide resin can be made optically clear (i.e., translucent or transparent) through a proper selection of suitable solvents. Generally, the amounts and types of solvents also are selected to provide a structure that is sufficiently strong and stable to permit its use as an applicator, and yet is capable of rubbing off onto the lips as a film ("ruboff").

The polyamide resin-based lipstick disclosed in U.S. Pat. No. 3,148,125 can be prone to syneresis, a phenomenon in which, at an elevated temperature, components including oils in the composition migrate out of (are exuded out of) the resin network, accumulate on the surface of the composition and, in severe cases, flow away from the composition. In a prior art lipstick, even after the temperature is lowered, the exuded components remain outside of the resin network or flow from the composition. The resulting network is left harder and less capable or incapable of ruboff, thus irreparably damaging the product. The '125 patent discloses that syneresis is controlled by the use of anhydrous lower aliphatic alcohols, in an amount from two to ten percent. Over time, however, volatile anhydrous lower aliphatic alcohols evaporate from the composition, leaving a harder composition that is less capable of rubbing off onto the lips as a film and also which is prone to syneresis. The use of volatile alcohols also contributes undesirable taste and smell components to the product.

While it is known to use specialized packaging for storage and shipping of volatile alcohol-containing lipsticks, and specialized containers for intermittent storage between periods of use to inhibit alcohol evaporation, these measures introduce materials and costs not otherwise necessary in typical lipstick products. Moreover, the use of specialized containers does not prevent evaporation of the volatile anhydrous lower aliphatic alcohols, but only retards the rate of evaporation and extends the period of time over which the lipstick product gradually becomes harder and less capable of ruboff. Similarly, while it is known to use flavor and scent additives to counteract the undesirable taste and smell of volatile alcohol, these additives merely mask, rather than eliminate, the taste and smell of the volatile alcohol.

Accordingly, it would be desirable to provide an optically clear polyamide resin-based composition that is not irreparably damaged by the effects of syneresis. It also would be desirable to provide an optically clear polyamide resin-based lipstick composition that does not require specialized packaging and storage containers to inhibit hardening and loss of ruboff ability.

SUMMARY OF THE INVENTION

It is an objective of the invention to overcome one or more of the problems described above.

Accordingly, one aspect of the invention is to provide a temperature-stable cosmetic composition including a polyamide resin, a solvent for the polyamide resin, and a gelling agent selected from the group consisting of N-acyl amino acid amides, N-acyl amino acid esters, and mixtures thereof, wherein the composition is translucent or transparent.

Another aspect of the invention is to provide a temperature-stable cosmetic composition that is essentially free of volatile alcohols.

Still another aspect of the invention is to provide a temperature-stable cosmetic composition including about 3 wt. % to about 15 wt. % of a polyamide resin; about 10 wt. % to about 40 wt. % of liquid castor oil; about 35 wt. % to about 45 wt. % of isoeicosane; about 1 wt. % to about 10 wt. % of polybutene; and about 0.1 wt. % to about 20 wt. % of a gelling agent having the formula:

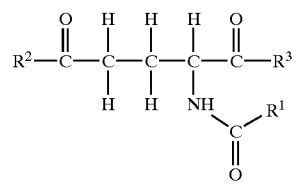

wherein $R^1$ is an alkyl, aryl, aralkyl radical having from about 6 to about 22 carbon atoms, and $R^2$ and $R^3$, independently, are an alkyl, aryl, aralkyl ester radical or amide radical in which the alkyl, aryl, aralkyl moiety has from about 2 to about 20 carbon atoms.

The compositions of the invention can be translucent or transparent, do not require specialized packaging or containers, are not subject to hardening caused by evaporation of volatile alcohols, are temperature-stable over a period of at least several weeks, and exhibit excellent esthetic and functional properties, including sensory properties, for consumer acceptance.

The invention also relates to temperature-stable compositions comprising an oil-soluble topically-active compound, such as an anti-inflammatory agent, and having the advantages of the invention. Such compositions further comprise a polyamide resin, a solid for the polyamide resin, a gelling agent selected from the group consisting of N-acyl amino acid amides, N-acyl amino acid esters, and mixtures thereof Such compositions can also be made translucent or transparent.

Further aspects and advantages of the invention may become apparent to those skilled in the art from a review of the following detailed description, taken in conjunction with the appended claims. While the invention is susceptible of embodiments in various forms, described hereinafter are specific embodiments of the invention with the understanding that the disclosure is illustrative, and is not intended to limit the invention to the specific embodiments described herein.

DETAILED DESCRIPTION OF THE INVENTION

A temperature-stable cosmetic composition of the invention includes a polyamide resin, a solvent for the polyamide resin, and a gelling agent selected from the group consisting of an N-acyl amino acid amide, an N-acyl amino acid ester, and mixtures thereof, wherein the composition is translucent or transparent. Preferably, the composition is essentially free of volatile alcohols, which eliminates the need for specialized packaging and containers for the composition, eliminates hardening of the composition caused by evaporation of volatile alcohols, and eliminates undesirable flavor and fragrance components.

When used as a lipstick, lip gloss, or lip balm product, the composition of the invention preferably is made from ingredients that have been approved for incidental ingestion.

The following detailed description generally illustrates lipstick compositions. However, in addition to the lipstick compositions, topically-effective compositions including an oil-soluble, topically-active compound; a polyamide resin; a solvent for the polyamide resin; and a gelling agent selected from the group consisting of N-acyl amino acid amides, N-acyl amino acid esters, and mixtures thereof, also demonstrate the improved attributes of the composition, including translucence or transparency and temperature-stability. Exemplary topically-effective compounds include topically-active drugs and medicaments, topical esthetics, additional skin-soothing emollients and other topical cosmetic compounds, topical anti-inflammatories, and the like. The invention also relates to such topically-effective compositions.

Various abbreviations used herein are defined as follows: ° C. is degree centigrade; atm is atmosphere; cm is centimeter; HLB is hydrophobic-lipophilic balance; Hg is mercury; mm is millimeter; rim is nanometer; and UV is ultraviolet.

The term "transparent" as used herein, unless otherwise specified, is intended to connote its usual dictionary definition. Thus, a transparent substance, like glass, allows ready viewing of objects behind the substance. A "translucent" substance allows light to pass through, but causes the light to be so scattered that it is impossible to clearly identify objects behind the translucent substance. For example, a composition is transparent if the maximum transmittance of light of any wavelength in the range about 200 rim to about 800 nm through a sample 10 cm thick is at least about 5%. Similarly, for example, a composition is translucent if such light through the sample is between about 0.01% and about 5%. The term "opaque" means that the maximum transmittance of such light is below about 0.01%. Transmittance can be easily measured by placing a sample of the composition having the required thickness in the light path of a TV-VIS Spectrophotometer such as the Hewlett-Packard 8451A Diode Ray Spectrophotometer. The advantage of this method of assessing transparency is that it is highly sensitive to optical clarity while independent of color.

The phrase "ambient conditions" as used herein, unless otherwise specified, refers to surrounding conditions at about one atmosphere of pressure (1 atm), at about 50% relative humidity, and at about 25° C.

The phrase "essentially free" as used herein, unless otherwise specified, is defined as meaning that the component (e.g., a volatile alcohol) is not intentionally added to the composition, but may be present in small amounts as a contaminant or as a by-product in an ingredient of the composition. Accordingly, a volatile alcohol can be present in a composition of the invention in an amount of 0.2% or less, by weight of the composition. The absence of a volatile alcohol reduces undesirable taste and odor components, eliminates the need for specialized packaging and containers, and eliminates hardening of the composition caused by evaporation of volatile alcohols.

The term "liquid" as used herein, unless otherwise specified, refers to a material that is amorphous (noncrystalline) at ambient conditions.

The term "volatile" as used herein, unless otherwise specified, refers to a material that is liquid at ambient conditions and that has a vapor pressure of at least about 2 mm of mercury (mmHg) at 25° C. The term "nonvolatile" as used herein, unless otherwise specified, refers to those materials which are not volatile as that term is defined herein.

The polyamide resin provides the composition with structure, while allowing the composition to have a transparent or translucent appearance.

As the amount of resin is decreased, the composition begins to lose clarity, while as the amount of resin is increased, the composition takes on an undesirable taste, which can be detrimental to a lipstick product. As the amount of resin is increased, the composition also becomes hard and loses the ability to rub off onto the lips or skin of a user. Thus, for a lipstick product or a product containing a topically-active compound, the polyamide resin preferably is present in the composition at about 2% to about 15%, more preferably about 5% to about 12%, or about 7% to about 12%, based on the total weight of the composition.

The polyamide resin must be soluble in a cosmetically-acceptable solvent at elevated temperatures and must solidify (i.e., form a gel solid) upon cooling. The polyamide resins that are useful in the invention preferably should be soluble in a suitable cosmetically-acceptable solvent at a temperature between about 50° C. and about 150° C., most preferably between about 50° C. and about 130° C. Given this temperature range, typically the preferred polyamide resins are not extensively covalently crosslinked, which would limit or prevent solubility. Suitable polyamide resins for use in the invention are classified as thermoplastics rather than thermosets.

Preferred polyamide resins for use in the invention are based on complex fatty acids, for example the VERSAMID series sold by Henkel Corp. or the UNIREZ series sold by Union Camp Corp. Polyamide resins based on terpolymers of simple nylons, such as Dupont Corporation's ELVAMIDE 8061, which is a terpolymer of nylon 6, nylon 66, and nylon 610, may also be suitable for use in the invention, for example when they are soluble in suitable cosmetically-acceptable solvents at a temperature between about 50° C. to about 150° C.

A preferred polyamide resin based on complex fatty acids includes a condensation product of a polycarboxylic acid with a diamnine (e.g., ethylenediamine, propylenediamine, or hexylenediamine), most preferably aliphatic diamines. Preferably, the polycarboxylic acid is a dicarboxylic acid, most preferably a dicarboxylic acid (e.g., adipic acid, oxalic acid, sebacic acid, and maleic acid). Polyamnide resins are described in Kirk-Othmer Encyclopedia of Chemical Technology, 4th Ed. (1993) at volume 8, pages 232–233, and in Ross et al. U.S. Pat. No. 5,500,209 (Mar. 19, 1996), the disclosures of which are hereby incorporated herein by reference.

The polyamide resin is a solid at room temperature, preferably composed primarily of polyamides of weight average molecular weight or weights in the range of about 1,000 to about 30,000 daltons, most preferably about 2,000 to about 10,000 daltons.

Preferred resins are the VERSAMID resins, particularly VERSAMID 930 polyamide resin, which is a condensation product of adipic acid and hexylenediamine. When using a polyamide resin such as VERSAMID in a translucent or transparent lipstick composition, the polyamide resin preferably is present in the composition at about 5% to about 12%, by weight of the composition, most preferably about 6% to about 10%, for example 7% by weight of the composition.

A suitable solvent for the polyamide resin modifies the polyamide resin to soften the resin and provide a composition with the desired firmness and transfer (ruboff) characteristics. A solvent for the polyamide resin can also function as a gloss agent, an emollient, a viscosity modifier, a vehicle for an optional component such as color, flavor, fragrance, sunscreen, and vitamin, and a co-solvent for components of the composition. The solvent for the polyamide need not be a single solvent, but also can be a solvent system including a plurality of solvents.

A suitable type and amount of solvent for the polyamide resin preferably are selected such that the polyamide resin can be dissolved therein at elevated temperatures, and yet can form a solid upon cooling. In the case of a lipstick, lip gloss, lip balm, or topically-active composition, a suitable type and amount of solvent for the polyamide resin preferably are selected such that a film of the polyamide resin-based composition can be transferred from the surface of the composition to the lips or skin of the user without compromising the structural integrity of the composition.

As the amount of the solvent is decreased, the appearance of the composition can change from transparent to translucent to opaque. The tactile characteristics of the composition also can change as the amount of solvent is decreased, such that the composition loses emolliency, becomes hard, and loses ruboff ability. When decreasing the content of certain solvents (e.g., polybutene and octyldodecanol), the composition also can lose a desirable wet, glossy appearance.

As the amount of solvent is increased, a detrimental result common with most solvents is the loss of structural integrity of the composition such that it does not function for its intended purpose, for example, as an applicator stick in the case of a lipstick, lip gloss, or lip balm. As the amount of solvent is increased, the composition may also exhibit undesirable tactile characteristics, such as tackiness in the case of a polybutene solvent. As the amount of certain solvents is increased, the appearance of the composition can change from transparent to translucent (such as in the case of octyldodecanol), and even opaque.

Thus, a solvent for the polyamide preferably is included in the composition at about 46% to about 97%, more preferably about 65% to about 97%, based on the total weight of the composition.

The solvent for the polyamide preferably is selected from the group consisting of unsaturated fatty alcohols (10–20 carbon atoms, branched or straight chain), such as oleyl alcohol or ricinoleic alcohol; saturated fatty alcohols (8–20 carbon atoms, branched or straight-chain), such as myristyl alcohol, lauryl alcohol, isolauryl alcohol, isostearyl alcohol, and isocetyl alcohol; fatty and/or aromatic carboxylic acid esters, such as benzyl benzoate, isostearyl benzoate, $C_{12}$–$C_{15}$ alkyl benzoates, $C_{10}$–$C_{15}$ alkyl lactates (including lauryl lactate), propylene glycol monolaurate, polyethylene glycol (400) monolaurate, liquid castor oil, isopropyl myristate, isopropyl palmitate, propyl myristate with the general formula RCOOR', where R and R' can be the same or different, and are from 2 to 20 carbon atoms, and can be saturated, unsaturated or aromatic; ethoxylated and/or propoxylated alcohols and acids, such as PPG-14 myristyl ether, PPG-14 butyl ether, PPG-3 myristyl ether, and myristeth-3 propionate; silicones such as cyclomethicones, dimethicones (50 to 1,000,000 cps) and functional silicones; mineral oils; branched-chain hydrocarbons, such as those sold under the trade name ISOPAR from Exxon Corporation, and those sold as PERMETHYL by Presperse, Inc., of South Plainfield, N.J. (e.g., isocicosane, sold as PERMETHYL 102A); and mixtures thereof.

Castor oil [CAS registry #8001-79-4] (liquid castor oil) is described in Kirk-Othmer Encyclopedia of Chemical Technology, 4th Ed. (1993) at volume 5, pages 301–320, the disclosure of which is hereby incorporated herein by reference. Castor oil is a triglyceride of various fatty acids, substantially all of which are unsaturated fatty acids. Castor oil esters are changed by hydrogenation from liquid products to soft waxes having melting points of about 45° C. to about 80° C. A castor oil suitable for use in a composition of the invention is a liquid product at room temperature, most preferably non-hydrogenated. Castor oil suitable for use in a composition of the invention is sold under its common name by Hansotech, Inc. of Woodbury, N.Y.

The solvent preferably is selected from the group consisting of fatty acid esters, fatty alcohols, mineral oils, branched-chain hydrocarbons, and mixtures thereof.

More preferably, the solvent for the polyamide resin is selected from the group consisting of liquid castor oil, propylene glycol monolaurate, polyethylene glycol (400) monolaurate, lauryl lactate, oleyl alcohol, isoeicosane, polybutene (also known as polyisobutylene, polybutylene, and polyisobutene) octyldodecanol, and mixtures thereof A polybutene product suitable for use in the invention is sold under the name INDOPOL H-100 by Amoco Chemical Company of Chicago, Ill., and is an isobutylene/butene copolymer (CAS #9003-29-6). An octyldodecanol (CAS #5333-42-6) product suitable for use in the invention is sold under the name EUTANOL G by M.M.P., Inc. of Plainfield, N.J., and contains 2-octyl dodecanol as a principal component. A fatty ester product suitable for use in the invention is sold under the name ULTRACAS G20 by B.F. Goodrich Performance Materials of Cleveland, Ohio. A particularly preferred blend of solvents includes liquid castor oil, polybutene, isoeicosane, and, optionally, octyldodecanol.

When a blend of solvents including liquid castor oil, polybutene, and isoeicosane is used as the solvent for the polyamide resin, liquid castor oil preferably is added at about 10% to about 40%, more preferably about 13% to about 28%; isoeicosane preferably is added at about 35% to about 45%, more preferably about 37% to about 43%; and polybutene preferably is added at about 1% to about 10%, more preferably about 3% to about 7%; all based on the weight of the composition. Optionally, the solvent for the polyamide resin includes octyldodecanol, preferably at about 15% to about 25%, more preferably at about 18% to about 23%, based on the weight of the composition.

It is theorized, but not relied upon herein, that the gelling agent acts to gel one or more components including an oil or solvent that are released from the polyamide resin as the temperature of the composition increases, and that the gelling agent subsequently releases gelled components for reabsorption back into the polyamide resin matrix upon cooling. Thus, it is theorized that as the amount of solvent in the composition increases, the amount of gelling agent should be increased in order to obtain the full advantages of the invention. Similarly, it is theorized that as the amount of solvent in the composition decreases, the amount of gelling agent could be decreased to avoid certain disadvantages such as reduction in transparency, and for cost savings.

As the amount of gelling agent in the composition decreases, composition loses the ability to resist irreversible syneresis. Thus, it is theorized that when a composition containing a polyamide resin and solvent according to the invention, but with low concentrations of gelling agent, is subjected to an increased temperature environment, components of the composition including oils irreversibly migrate out of the resin matrix and collect at the surface of the composition. When such a composition is cooled, the exuded components are not reabsorbed into the resin matrix.

On the other hand, as the amount of gelling agent in the composition increases, the composition can change from transparent to translucent and even opaque. Moreover, using more than a suitable amount of gelling agent provides no additional benefit from a syneresis standpoint, and only serves to increase cost of the composition.

Thus, a gelling agent preferably is included in the composition at about 0.1% to about 20%, more preferably about 1% to about 10%, most preferably about 3% to about 7%, based on the total weight of the composition.

The gelling agent is selected from the group consisting of N-acyl amino acid amides, N-acyl amino acid esters, and mixtures thereof. For example, N-acyl glutamic acid diamide is sold as oil gelatinization agent GP-1 by Anjinomoto Co. Inc., of Tokyo, Japan. Generally, N-acyl amino acid gelling agents are described in Saito et al. U.S. Pat. No. 3,969,087 (Jul. 13, 1976), the disclosure of which is hereby incorporated herein by reference.

Preferably, the gelling agent has the formula:

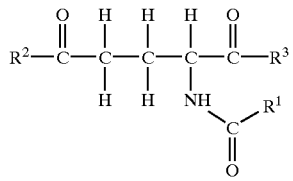

wherein $R^1$ is an alkyl, aryl, aralkyl radical having from about 6 to about 22 carbon atoms, and $R^2$ and $R^3$, independently, are an alky, aryl, aralkyl ester radical or amide radical in which the alkyl, aryl, aralkyl moiety has from about 2 to about 20 carbon atoms.

The term "alkyl" as used herein is a hydrocarbon group containing the indicated number of carbon atoms and includes straight chained and branched alkyl or alkylene groups, typically methyl, ethyl, and straight chain and branched propyl, propylene, and butyl groups.

The term "aryl" as used herein refers to optionally substituted 5- or 6-membered carbocyclic and heterocyclic aromatic groups, including, but not limited to, phenyl, thienyl, fliryl, pyrryl, imidazolyl, pyrimidyl, and pyridyl. The term "aralkyl" as used herein refers to an aryl group having a $C_{1-15}$ alkyl substituent.

More preferably, a gelling agent is selected from the group consisting of N-lauroyl glutamic acid diethylamide, N-lauroyl glutamic acid dibutylamide, N-lauroyl glutamic acid dihexylamide, N-lauroyl glutamic acid dioctylamide, N-lauroyl glutamic acid didecylamide, N-lauroyl glutamic acid ditetradecylamide, N-lauroyl glutamic acid dihexadecylamide, N-lauroyl glutamic acid distearylamide, N-stearoyl glutamic acid dibutylamide, N-stearoyl glutamic acid dihexylamide, N-stearoyl glutamic acid diheptylamide, N-stearoyl glutamic acid dioctylamide, N-stearoyl glutamic acid didecylamide, N-stearoyl glutamic acid didodecylamide, N-stearoyl glutamic acid ditetradecylamide, N-stearoyl glutamic acid dihexadecylamide, N-stearoyl glutamic acid distearylamide, and mixtures thereof.

Most preferably, the gelling agent includes N-lauroyl glutamic acid dibutylamide.

In accordance with another feature of the invention, a temperature-stable composition useful as a lipstick, lip gloss, lip balm, or topically active composition is provided. The lipstick composition is temperature-stable over a period of several weeks, imparts a high gloss, highly emollient film to the user's lips, and can also be made transparent.

The temperature-stable cosmetic composition includes about 3 wt. % to about 15 wt. % of a polyamide resin; about 10 wt. % to about 40 wt. % of liquid castor oil; about 35 wt. % to about 45 wt. % of isoeicosane; about 1 wt. % to about 10 wt. % of polybutene; and about 0.1 wt. % to about 20 wt. % of a gelling agent having the formula:

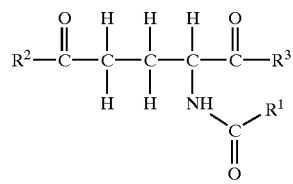

wherein $R^1$ is an alkyl, aryl, aralkyl radical having from about 6 to about 22 carbon atoms, and $R^2$ and $R^3$, independently, are an alkyl, aryl, aralkyl ester radical or amide radical in which the alkyl, aryl, aralkyl moiety has from about 2 to about 20 carbon atoms.

In accordance with another feature of the invention, a wide variety of oil-soluble, topically-active compounds can be incorporated into a composition of the invention. Preferably, the oil-soluble, topically-active compounds are be incorporated into a composition of the invention in an amount of about 0.01% to about 30%, more preferably about 0.1% to about 20%, and even more preferably about 1% to about 10%, by weight of the composition. Such topically-active compositions include both cosmetic and medicinal compounds that act upon contact with the skin.

The topically-active compound can be a cosmetically-active compound, a medically-active compound or any other compound that is useful upon application to the skin. Such topically-active compounds include sunscreen compounds, vitamins (including vitamins, A, D, and E), antibacterial compounds, antifungal compounds, anti-inflammatory compounds, topical anesthetics and other cosmetic and medical topically-active compounds.

Therefore, in accordance with another feature of the invention, the transparent or translucent topically-effective composition can include any of the above-described compounds. A topically-active compound can be included in a composition of the invention in an amount sufficient to perform its intended function. For example, oil-soluble topically-active drugs, such as analgesics; antibacterials and antiseptics; antifungal compounds; anti-inflammatory compounds; antiparasitics; topical anesthetics; bum relief ointments; depigmenting agents; dermatologicals; diaper rash relief agents; skin rash, skin disease and dermatitis medications; herpes treatment drugs; pruritic medications; psoriasis, seborrhea and scabicide agents; and anti-itch and irritation-reducing compounds can be incorporated in a composition of the invention in an amount sufficient to perform its intended function.

In addition to the polyamide resin, solvent, and gelling agent, a composition of the invention optionally and preferably includes a surfactant (surface active agent), which can also be a blend of surfactants. The surfactant acts as a viscosity modifier or thickener, reduces the susceptibility of the composition to syneresis, and improves the texture of the composition.

Thus a surfactant preferably is included in the composition at about 0% to about 20%, and more preferably about 1% to about 12%, by weight of the composition. Preferably the surfactant is a nonionic surfactant or a nonionic surfactant blend having an HLB value of about 3 to about 20. Most preferably, the surfactant is present in an amount of about 3% to about 8%, by weight of the composition.

The "HLB value," or hydrophobic-lipophilic balance value, of a surfactant is a term well-known to those skilled in the art. The HLB value is related to the solubility of the surfactant, wherein a surfactant with a low HLB value, i.e., about 10 or less, tends to be oil-soluble and a surfactant with a high HLB value, i.e., greater than about 10, tends to be water-soluble.

To achieve the full advantage of the invention, a composition of the invention preferably includes a nonionic surfactant having an HLB of about 7 to about 10, or a nonionic surfactant blend comprising a first nonionic surfactant having an HLB value of about 10 or greater and a second nonionic surfactant having an HLB of less than about 10, wherein the nonionic surfactant blend has an HLB of about 7 to about 10.

Preferred nonionic surfactants or nonionic surfactant blends have an HLB value of about 7 to about 10 and tend to be lipophilic, and therefore oil-soluble.

A nonionic surfactant having an HLB value of about 3 to about 20, and preferably 7 to about 10, can be used alone as the nonionic surfactant of the invention. Nonionic surfactants having an HLB value of at least about 10 also can be used as the first surfactant of a nonionic surfactant blend having an HLB value of about 7 to about 10. Typically, nonionic surfactants having an HLB value of at least about 10 have a hydrophobic base, such as a long chain alkyl group or an alkylated aryl group, and a hydrophilic chain comprising a sufficient number of ethoxy and/or propoxy moieties.

A nonionic surfactant having an HLB of less than about 10 is the second nonionic surfactant of the nonionic surfactant blend having an HLB of about 7 to about 10. The nonionic surfactants having an HLB of less than about 10 typically have the same type hydrophobic base as the high HLB surfactants, but include fewer ethoxy and/or propoxy moieties.

The HLB value of a particular nonionic surfactant can be found in McCutcheon's Emulsifiers and Detergents, North American and International Editions, MC Publishing Co., Glen Rock, N.J. (1993) (hereinafter McCutcheon's). Alternatively, the HLB value of a particular nonionic surfactant can be estimated by dividing the weight percent of oxyethylene in the surfactant by five (for surfactants including only ethoxy moieties). In addition, the HLB value of a nonionic surfactant blend can be determined by the following formula:

$$HLB = (\text{wt. \% A})(HLB_A) + (\text{wt. \% B})(HLB_B)$$

wherein wt. % A and wt. % B are the weight percent of nonionic surfactants A and B in the nonionic surfactant blend, and $HLB_A$ and $HLB_B$ are the HLB values for nonionic surfactants A and B respectively.

Exemplary classes of suitable nonionic surfactants include, but are not limited to, polyoxyethylene ethers of fatty ($C_6$–$C_{22}$) alcohols, polyoxypropylene ethers of fatty ($C_6$–$C_{22}$) alcohols, dimethicone copolyols, ethoxylated alkylphenols, polyethylene glycol ethers of methyl glucose, polyethylene glycol ethers of sorbitol, fatty ($C_6$–$C_{22}$) acid esters of anhydrosorbitol, ethoxylated sorbitan fatty acid esters, and mixtures thereof.

Exemplary nonionic surfactants having an HLB value of 10 or greater that can be used alone or in the nonionic surfactant blend include, but are not limited to methyl gluceth-20, methyl gluceth- 10, PEG-20 methyl glucose distearate, PEG-20 methyl glucose sesquistearate, PEG-200 castor oil, $C_{11\text{-}15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene- 10 stearyl ether, polyoxyethylene-20 cetyl ether, polyoxyethylene-21 stearyl ether, polyoxyethylene- 10 oleyl ether, polyoxyethylene-20 oleyl ether, an ethoxylated nonylphenol, ethoxylated octylphenol, ethoxylated dodecylphenol or ethoxylated fatty ($C_6$–$C_{22}$) alcohol including at least 9 ethylene oxide moieties, polyoxyethylene-20 iso-hexadecyl ether, dimethicone copolyol, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, polysorbate 80 (for example, LIPOSORB O-20, sold by Lipo Chemicals, Inc., of Paterson, N.J.), and mixtures thereof.

Exemplary nonionic surfactants having an HLB value of less than 10 that can be used in the nonionic surfactant blend, include, but are not limited to, laureth-2, laureth-3, laureth-4, PEG-3 castor oil, an ethoxylated nonylphenol, ethoxylated octylphenol, ethoxylated dodecylphenol or ethoxylated fatty ($C_6$–$C_{22}$) alcohol having less than 9 ethylene oxide moieties, PEG 600 dioleate, PEG 400 dioleate, sorbitan oleate (for example LIPOSORB O, sold by Lipo Chemicals, Inc., of Paterson, N.J.), sorbitan monoleate, and mixtures thereof.

Numerous other nonionic surfactants having an HLB value of either about 10 or greater, or less than about 10 are disclosed in McCutcheon's at pages 1–246 and 266–272; in the CTFA International Cosmetic Ingredient Dictionary, Fourth Ed., Cosmetic, Toiletry and Fragrance Association, Washington, D.C. (1991) (hereinafter the CTFA Dictionary) at pages 1–651; and in the CTFA Handbook, at pages 86–94, each incorporated herein by reference.

In addition to nonionic surfactants, anionic or cationic surfactants can be used as the surfactant. Exemplary anionic surfactants, such as salts of fatty ($C_8$–$C_{22}$) acids, are disclosed in McCutcheon's at pages 263–266, incorporated herein by reference. Exemplary cationic surfactants are disclosed in McCutcheon's at pages 272–273, incorporated herein by reference.

The compositions of the invention also can comprise additional, optional components to provide desirable properties. Suitable optional ingredients include, but are not limited to, preservatives, color, flavor, and fragrance components, pearlescent agents, glitter agents, sparkle agents, sunscreens, UV absorbers, vitamins, texture enhancers, fillers, and other suitable agents, especially agents suitable for use in a lipstick, lip gloss, lip balm, or a topically-active composition.

In certain cases, it may be desirable to add lower aliphatic alcohols to a composition of the invention to further inhibit syneresis, for example in products that do not permit or require reuse after breaking the seal of a package or container, or in special use environments or products where syneresis may be an acute problem. In such cases, a lower aliphatic alcohol ($C_1$–$C_8$, branched or straight-chain) preferably is used in the composition of the invention at 0% to about 10%, more preferably about 0.1% to about 5%, most preferably less than 2%, by weight of the composition. A lower aliphatic alcohol suitable for use in a composition of the invention is isopropyl alcohol, sold under its common name as a 99% solution by Research Solvents and Chemicals, Inc.

It may be desirable to add one or more preservatives or antioxidants to a composition of the invention. As the concentration of preservative is increased, it is increasingly difficult to solubilize the preservative and the preservative may irritate the skin, whereas when the concentration of preservative is decreased it becomes less effective. Thus, a suitable preservative preferably is included in the composition at about 0.01% to about 0.5%, more preferably about 0.05% to about 0.2%, for example 0.1%, by weight of the composition. Suitable preservatives include oil-soluble preservatives such as propyl paraben, butyl paraben, mixtures thereof, and isoforms thereof, as well as BHA and BHT. Propyl paraben is most preferred. Propyl paraben suitable for use in a composition of the invention is sold under its common name by Acme-Hardesty Co. of Jenkintown, Pa.

It also may be desirable to add one or more color components to the composition, especially for use as a lipstick product. A composition of the invention including a polyamide resin, solvent, and gelling agent typically has a slight yellow tinge in the absence of color agents, and can be formulated to be highly transparent. At elevated amounts of color components, the composition of the invention can change from transparent to translucent and even opaque. Thus, to make a translucent or transparent composition of the invention, a suitable color agent preferably is included in the composition at about 0% to about 2%, more preferably about 0% to about 0.5%, for example 0.02%, by weight of the composition. A variety of coloring agents suitable for use in lipstick, lip gloss, and lip balm compositions can be used to color a composition of the invention, including inorganic and organic dyes, pigments, and lakes, both oil-soluble and oil-insoluble. Generally, color agents include D & C's (including Red #6 and Ba Lake, Red #7 and Ca Lake, Red #21 and Al Lake, Red #27 and Al Lake, Red #33 and Al Lake, Red #30, Red #36, and Yellow #10), F D & C's (including Yellow #5 and 6 and Al Lake; Blue #1 and Al Lake), titanium dioxide (including pigmentary and ultrafine), iron oxides (including pigmentary and ultrafine), zinc oxide (including pigmentary and ultrafine), ultramarines, magnesium violet, ferrous blue, chromium greens, and carmine. Suitable color agents for use in compositions of the invention, including Red #17, are available from Warner Jenkinson Inc. of St. Louis, Mo.

Optionally, other agents can be added to affect the visual character of a composition of the invention. Such agents include pearlescent materials (including guanine, bismuth oxychloride, mica, titanium dioxide coated mica, and iron oxide coated mica), flourescent agents, and glitter and sparkle agents (which are discrete particles that can be made from coated plastics). Generally, these agents can be added to a composition of the invention in the same concentrations as color agents.

It also may be desirable to add one or more flavor and fragrance components to the composition. At low levels of flavor and fragrance components, their presence is imperceptible to the human senses, whereas at elevated levels, a composition of the invention may be detrimentally affected by a change from transparent to translucent and even opaque and by loss of structural integrity. In addition, at elevated levels flavor and fragrance components may act as irritants to human skin. Thus, to make a translucent or transparent composition of the invention, at least one of a suitable flavor and fragrance agent preferably is included in the composition at about 0% to about 5%, more preferably about 0% to about 2%, for example 1%, by weight of the composition. A variety of flavor and fragrance agents suitable for use in cosmetic compositions can be used in a composition of the invention. Suitable flavor ingredients are available from Flavor Sciences of Ossining, N.Y.

A particularly preferred flavor agent is sodium saccharine, preferably solvated in propylene glycol. When used in conjunction with a flavor or fragrance component, sodium saccharine functions to boost the sensory impact of the flavor or fragrance component. At lower concentrations, the effect is imperceptible, whereas at higher concentrations the effect can be overbearing. Thus, when used, sodium saccharine preferably is included at about 0% to about 0.1%, more preferably about 0.02 to about 0.06%, for example 0.05%, based on the weight of the composition. A suitable sodium saccharine is sold as a 20% solution of sodium saccharine in propylene glycol, available from Universal Preservachem Inc. of Edison, N.J.

It may be desirable to include one or more vitamins to the composition of the invention. At low concentrations, vitamins generally are ineffective, whereas at higher concentrations a composition of the invention can be detrimentally affected by a change from transparent to translucent and even opaque and by loss of structural integrity. Thus, when used, vitamin preferably is included at about 0.01% to about 5%, more preferably about 0.1 to about 3%, for example 1%, based on the weight of the composition. Preferred vitamins include oil-soluble vitamins, such as vitamin A, vitamin D, and vitamin E.

A safe and effective amount of sunscreen agent and a UV absorber can be used in a composition of the invention. At low concentrations, sunscreen agents and UV absorbers are less effective, whereas at higher concentrations a composition of the invention can be detrimentally affected by a change from transparent to translucent and even opaque and by loss of structural integrity. Thus, when used, at least one of a sunscreen agent and UV absorber preferably is included at about 0.1% to about 10%, more preferably from about 1% to about 5%, by weight of the composition of the invention. Exact amounts will vary depending upon the sunscreen chosen and the desired Sun Protection Factor (SPF).

Suitable sunscreen compositions for use on human skin are known to those in the art and include, but are not limited to, octyl methoxycinnamate, benzophenone-3, butyl methoxydibenzoylmethane, oxybenzone, PABA and PABA derivatives. Various other sunscreen materials are found in "A Survey of Ultraviolet Absorbers in Commercially Available Sun Products," by Roelandts, et al., International Journal of Dermatology, Vol. 22, pages 247–55 (May 1985) and the CTFA Cosmetic Ingredient Handbook, J. M. Nikitakis, Ed., 1st Edition, pages 86–87 (1988), the disclosures of which are hereby incorporated herein by reference. Compositions of the invention can also include a diester and/or polyester of a naphthalene dicarboxylic acid that photostabilizes sunscreen components.

Suitable NV absorbers are known to those in the art and include, but are not limited to, allantoin PABA, butyl methoxydibenzoylmethane, ethyl diusopropylcinnamate, octyl methoxycinnamate, octyl salicylate, and PABA. Various other NV absorbers can be found in the CTFA Cosmetic Ingredient Handbook, J. M. Nikitakis, Ed., 1 st Edition, page 98 (1988), the disclosure of which is hereby incorporated herein by reference. Octyl salicylate is preferred, and has little affect on the clarity of the composition. A suitable octyl salicylate product is sold under the name ESCALOL 587 by ISP Van Dyk of Belleville, N.J.

A composition of the invention can be prepared by any suitable method, or by the following process which forms part of the invention. All components with a decomposition temperature higher than the melting point of the highest melting component are added to vessel, and the vessel is heated to a temperature greater than the temperature of the highest melting component and below the decomposition temperature of any component in the vessel ("high mixing temperature"; typically greater than about 100° C., preferably about 130° C. to about 150° C.), and stirred until homogeneous, typically for about 30 minutes. Generally, these components include the polyamide resins, oil-based solvents, and gelling agent, which is typically the highest melting component. Preferably, the vessel is closed or covered to prevent loss of components that are volatile at the high mixing temperature.

Next, the mixture is cooled to a temperature near, (e.g., within about 10° C.) but greater than, the set point of the mixture ("low mixing temperature"), and the majority of the remaining components are added and mixed until all soluble components are solubilized and all non-soluble components are homogeneously dispersed, typically for several hours, before filling containers. Components that are highly volatile at this mixing temperature and components that are prone to degradation at this temperature, such as suncreens, UV blockers, vitamins, flavor and fragrance components, and sodium saccharine, are not added until just prior to (e.g., within minutes of) the filling step.

To fill lipstick containers, the mixture is pumped into lipstick molds, and then rapidly chilled to below the setpoint of the mixture, typically in about 1 minute. To make a completed product such as a lipstick, lip gloss or lip balm, the chilled composition is assembled into a suitable applicator case, such as a conventional lipstick case or pan. Specialized containers designed to prevent loss of volatile lower alcohols are not required when a volatile lower alcohol is not added to the composition, and for products that do not permit or require reuse after breaking the seal of a package or container.

In a preferred method of the invention, one or more solvents (preferably liquid castor oil) is pre-blended with one or more color agents to produce a homogenous, color pre-blend, which is subsequently added to the mixture at the low mixing temperature in an appropriate ratio. This expedient reduces the mixing time required to produce a homogenized composition.

EXAMPLES

The following examples are provided to illustrate the invention but are not intended to limit the scope of the invention.

Examples 1–5

Transparent or Translucent Lipgloss Compositions with Surfactant and Essentially Free of Volatile Alcohols

| Ingredient | Trade Name and/or Supplier | % of Composition (by weight) | | | | |
|---|---|---|---|---|---|---|
| | | Ex. 1 | Ex. 2 | Ex. 3 | Ex. 4 | Ex. 5 |
| polyamide resin | VERSAMID 930 | 7.00 | 8.00 | 7.00 | 7.00 | 7.00 |
| castor oil (liquid, non-hydrogentated) | Hansotech Inc. | 18.00 | 18.30 | 18.30 | 18.53 | 18.76 |
| polybutene | INDOPOL H-100 | 5.00 | 5.00 | 5.00 | 5.00 | 5.00 |
| isoeicosane | PERMETHYL 102A | 38.88 | 38.41 | 39.41 | 39.91 | 40.41 |
| N-acyl glutamic acid diamine | Anjinomoto GP-1 | 5.00 | 4.00 | 4.00 | 3.00 | 2.00 |
| octyldodecanol | EUTANOL G | 21.00 | 21.17 | 21.17 | 21.44 | 21.71 |
| sorbitan oleate | LIPOSORB O | 2.50 | 2.50 | 2.50 | 2.50 | 2.50 |
| polysorbate 80 | LIPOSORB O-20 | 2.50 | 2.50 | 2.50 | 2.50 | 2.50 |
| propyl paraben | Acme-Hardesty Co. | 0.10 | 0.10 | 0.10 | 0.10 | 0.10 |
| Red #17 | Warner Jenkinson Inc. | 0.02 | 0.02 | 0.02 | 0.02 | 0.02 |

Each composition was prepared by the following method. Castor oil, octyldodecanol, and polybutene were added to a closed vessel and briefly mixed. Next, polyamide resin and N-acyl glutamic acid diamide powder were added and the vessel was heated to about 130° C. Mixing continued until the resin and N-acyl glutamic acid diamide were fully dissolved, about 30 minutes total time.

Next the mixture was cooled until it reached about 90° C. (about two hours), and then polysorbate 80, sorbitan monoleate, isoeicosane, propylparaben, and a preblend of Red #17 and castor oil were added. The resulting mixture was mixed until all soluble components were solubilized and all non-soluble components were homogeneously dispersed (about four hours).

Finally the mixture was pumped into lipgloss molds and rapidly chilled to below the set point of about 82° C. (elapsed time of about one minute), and the lipgloss compositions were assembled into typical lipgloss cases.

The resulting lipgloss compositions were transparent or translucent, exhibited a smooth, moist texture, a high gloss, and a structure sufficiently strong and stable to permit use as an applicator and yet easily capable of rubbing off onto the lips as a film. Moreover, the compositions did not have any perceptible volatile alcohol taste or scent.

Examples 6–9

Transparent or Translucent Lipgloss Compositions Without Sorbitan Oleate and Polysorbate 80 Surfactants and Essentially Free of Volatile Alcohols

| Ingredient | Trade Name and/or Supplier | % of composition (by weight) | | | |
|---|---|---|---|---|---|
| | | Ex. 6 | Ex. 7 | Ex. 8 | Ex. 9 |
| polyamide resin | VERSAMID 930 | 8.00 | 8.00 | 9.00 | 10.00 |
| castor oil (liquid; non-hydrogentated) | Hansotech Inc. | 19.00 | 19.00 | 19.00 | 19.00 |

|  | Trade Name | % of composition (by weight) | | | |
|---|---|---|---|---|---|
| Ingredient | and/or Supplier | Ex. 6 | Ex. 7 | Ex. 8 | Ex. 9 |
| polybutene | INDOPOL H-100 | 5.08 | 5.08 | 5.08 | 5.08 |
| isoeicosane | PERMETHYL 102A | 40.80 | 41.80 | 41.80 | 41.80 |
| N-acyl glutamic acid diamide | Anjinomoto GP-1 | 5.00 | 4.00 | 3.00 | 2.00 |
| octyldodecanol | EUTANOL G | 22.00 | 22.00 | 22.00 | 22.00 |
| propyl paraben | Acme-Hardesty Co. | 0.10 | 0.10 | 0.10 | 0.10 |
| Red #17 | Warner Jenkinson Inc. | 0.02 | 0.02 | 0.02 | 0.02 |

The compositions were prepared as in Examples 1–5, except that neither sorbitan oleate nor polysorbate 80 was added to the composition. The resulting lipgloss compositions were transparent or translucent, exhibited a smooth, moist texture, a high gloss, and a structure sufficiently strong and stable to permit use as an applicator and yet easily capable of rubbing off onto the lips as a film.

Examples 10–14

Transparent or Translucent Lipgloss Compositions With Surfactant and Volatile Alcohol

|  |  | % of composition (by weight) | | | | |
|---|---|---|---|---|---|---|
| Ingredient | Trade Name and/or Supplier | Ex. 10 | Ex. 11 | Ex. 12 | Ex. 13 | Ex. 14 |
| polyamide resin | VERSAMID 930 | 7.00 | 8.00 | 7.00 | 7.00 | 7.00 |
| castor oil liquid; non-hydrogenated) | Hansotech Inc. | 17.83 | 18.07 | 18.07 | 18.30 | 18.53 |
| polybutene | INDOPOL H-100 | 5.00 | 5.00 | 5.00 | 5.00 | 5.00 |
| isoeicosane | PERMETHYL 102A | 38.41 | 37.91 | 38.91 | 39.41 | 39.91 |
| N-acyl glutamic acid diamide | Anjinomoto GP-1 | 5.00 | 4.00 | 4.00 | 3.00 | 2.00 |
| octyldodecanol | EUTANOL G | 20.64 | 20.90 | 20.90 | 21.17 | 21.44 |
| sorbitan oleate | LIPOSORB O | 2.50 | 2.50 | 2.50 | 2.50 | 2.50 |
| polysorbate 80 | LIPOSORB O-20 | 2.50 | 2.50 | 2.50 | 2.50 | 2.50 |
| propyl paraben | Acme-Hardesty Co. | 0.10 | 0.10 | 0.10 | 0.10 | 0.10 |
| Red #17 | Warner Jenkinson Inc. | 0.02 | 0.02 | 0.02 | 0.02 | 0.02 |
| isopropyl alcohol, 99% | Research Solvents and Chemicals, Inc. | 1.00 | 1.00 | 1.00 | 1.00 | 1.00 |

The compositions were prepared as in Example 1–5, except that isopropyl alcohol was added just prior to filling. The resulting lipgloss compositions were transparent or translucent, exhibited a smooth, moist texture, a high gloss, and a structure sufficiently strong and stable to permit use as an applicator and yet easily capable of rubbing off onto the lips as a film.

Examples 15–16

Transparent or Translucent Lipgloss Compositions With Sunscreen and Flavor

| Ingredient | Trade Name and/or Supplier | % of composition (by weight) | |
|---|---|---|---|
|  |  | Ex. 15 | Ex. 16 |
| polyamide resin | VERSAMID 930 | 8.00 | 8.00 |
| castor oil liquid; non-hydrogenated) | Hansotech Inc. | 10.00 | 10.00 |
| polybutene | INDOPOL H-100 | 5.00 | 5.00 |
| isoeicosane | PERMETHYL 102A | 31.88 | 31.63 |
| N-acyl glutamic acid diamide | Anjinomoto GP-1 | 4.00 | 4.00 |
| octyldodecanol | EUTANOL G | 20.00 | 20.00 |
| sorbitan oleate | LIPOSORB O | 2.50 | 2.50 |
| polysorbate 80 | LIPOSORB O-20 | 2.50 | 2.50 |
| propyl paraben | Acme-Hardesty Co. | 0.10 | 0.10 |
| Red #17 | Warner Jenkinson Inc. | 0.02 | 0.02 |
| octyldodecyl ricinoleate | ULTRACAS G20 | 10.00 | 10.00 |
| raspberry flavor | Flavor Sciences | 1.00 | 1.00 |
| octyl salicylate | ESCALOL 587 | 5.00 | 5.00 |
| sodium saccharin solution (20 % by weight in propylene glycol) | Universal Preservachem Inc. |  | 0.25 |

The compositions were prepared as in Example 1–5, except that octyl salicylate, raspberry flavor, and sodium saccharin solution were added just prior to filling. The resulting lipgloss compositions were transparent or translucent, exhibited a smooth, moist texture, a high gloss, and a structure sufficiently strong and stable to permit use as an applicator and yet easily capable of rubbing off onto the lips as a film.

Example 17

Syneresis Stability Testing

Syneresis stability testing was performed on the compositions of Examples 1 through 16. Each sample was placed in a cup to prevent loss of sample, and placed in a laboratory oven for heating. The appearance of each sample was visually observed and evaluated at the beginning of each test period at room temperature ($RT_1$, about 22° C.), again when the sample reached 45° C., and again when the sample cooled to room temperature ($RT_2$, about 22° C.). Recorded observations correspond to the following scale of "sweat factors": 0=none; 1=glossy surface; 2=liquid beads on surface; 3=exuded component running down surface into cup; 4=product into bottom of cup; 5=excessive product. Results are tabulated below.

| Formula | Day 1 RT₁ | 45° C. | RT₂ | Week 1 RT₁ | 45° C. | RT₂ | Week 2 RT₁ | 45° C. | RT₂ | Week 3 RT₁ | 45° C. | RT₂ | Week 4 RT₁ | 45° C. | RT₂ |
|---|---|---|---|---|---|---|---|---|---|---|---|---|---|---|---|
| Ex. 1 | 0 | 2 | 0 | 0 | 2 | 0 | 0 | 2 | 0 | 0 | 2 | 0 | 0 | 2 | 0 |
| Ex. 2 | 1 | 1 | 0 | 1 | 2 | 0 | 1 | 1 | 0 | 0 | 0 | 0 | 0 | 0 | 0 |
| Ex. 3 | 1 | 1 | 0 | 1 | 2 | 0 | 1 | 2 | 0 | 1 | 2 | 0 | 1 | 2 | 0 |
| Ex. 4 | 1 | 0 | 0 | 1 | 0 | 0 | 1 | 1 | 0 | 1 | 1 | 0 | 1 | 0 | 0 |
| Ex. 5 | 2 | 3 | 1 | 2 | 3 | 0 | 2 | 3 | 0 | 2 | 0 | 0 | 2 | 1 | 0 |
| Ex. 6 | 2 | 3 | 0 | 0 | 2 | 0 | 0 | 1 | 0 | 0 | 1 | 0 | 0 | 2 | 0 |
| Ex. 7 | 1 | 1 | 0 | 1 | 0 | 0 | 1 | 1 | 0 | 1 | 1 | 0 | 1 | 0 | 0 |
| Ex. 8 | 1 | 0 | 0 | 1 | 0 | 0 | 1 | 1 | 0 | 1 | 1 | 0 | 1 | 0 | 0 |
| Ex. 9 | 2 | 4 | 2 | 2 | 4 | 1 | 2 | 4 | 2 | 2 | 4 | 1 | 2 | 4 | 0 |
| Ex. 10 | 0 | 2 | 0 | 0 | 2 | 0 | 0 | 1 | 0 | 0 | 1 | 0 | 0 | 0 | 0 |
| Ex. 11 | 0 | 0 | 0 | 0 | 1 | 0 | 0 | 0 | 0 | 0 | 0 | 0 | 0 | 0 | 0 |
| Ex. 12 | 0 | 0 | 0 | 0 | 0 | 0 | 0 | 0 | 0 | 0 | 0 | 0 | 0 | 0 | 0 |
| Ex. 13 | 1 | 1 | 0 | 1 | 1 | 0 | 2 | 1 | 0 | 1 | 1 | 0 | 1 | 0 | 0 |
| Ex. 14 | 1 | 1 | 0 | 1 | 1 | 0 | 1 | 1 | 0 | 1 | 0 | 0 | 1 | 1 | 0 |
| Ex. 15 | 0 | 2 | 0 | 0 | 2 | 0 | 0 | 2 | 0 | 0 | 2 | 0 | 0 | 2 | 0 |
| Ex. 16 | 0 | 1 | 0 | 0 | 2 | 0 | 1 | 1 | 0 | 0 | 1 | 0 | 0 | 1 | 0 |

The results show that all formulations except those of Examples 5, 6, and 9 provide compositions that resist syneresis at 45° C. and which, upon cooling, return to compositions that do not exhibit exuded components. All formulations except those of Examples 5, 6, and 9, even after 5 cycles of heating and cooling, provided compositions that were transparent or translucent, exhibited smooth, moist texture, high gloss, and had structure sufficiently strong and stable to permit its use as an applicator, yet easily capable of rubbing off onto the lips as a film.

The formulations of Examples 5, 6, and 9 have utility as lipgloss products useful in environments where their temperature would not be elevated to the point where they would be damaged. Similar formulations are also useful in other products, such as compositions including topically-active compounds.

The foregoing description is given for clearness of understanding only, and no unnecessary limitations should be understood therefrom, as modifications within the scope of the invention may be apparent to those having ordinary skill in the art.

What is claimed is:

1. A temperature-stable cosmetic composition comprising:
   a. a polyamide resin;
   b. a solvent for the polyamide resin comprising a mixture of liquid castor oil, isoeicosane, and polybutene; and
   c. a gelling agent selected from the group consisting of N-acyl amino acid amides, N-acyl amino acid esters, and mixtures thereof;
   wherein said composition is translucent or transparent.

2. The composition of claim 1 comprising about 65 wt. % to about 97 wt. % of said solvent.

3. The composition of claim 1 comprising about 10 wt. % to about 40 wt. % of liquid castor oil.

4. The composition of claim 1 comprising about 35 wt. % to about 45 wt. % of isoeicosane.

5. The composition of claim 1 comprising about 1 wt. % to about 10 wt. % of polybutene.

6. The composition of claim 1 further comprising octyldodecanol.

7. The composition of claim 6 comprising about 15 wt. % to about 25 wt. % octyldodecanol.

8. The composition of claim 1, further comprising an oil-soluble, topically-active compound.

9. The composition of claim 8 comprising about 3 wt. % to about 8 wt. % of a surface active agent.

10. The composition of claim 9 wherein said surface active agent is nonionic.

11. The composition of claim 9 wherein said surface active agent has a HLB of about 8 to about 11.

12. A temperature-stable cosmetic composition comprising:
   a. about 3 wt. % to about 15 wt. % of a polyamide resin;
   b. about 10 wt. % to about 40 wt. % of liquid castor oil;
   c. about 35 wt. % to about 45 wt. % of isoeicosane;
   d. about 1 wt. % to about 10 wt. % of polybutene; and
   e. about 0.1 wt. % to about 20 wt. % of a gelling agent having the formula:

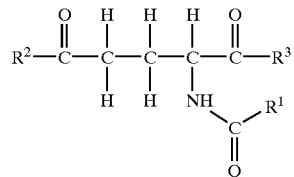

wherein $R^1$ is an alkyl, aryl, aralkyl radical having from about 6 to about 22 carbon atoms, and $R^2$ and $R^3$, independently, are an alkyl, aryl, aralkyl ester radical or amide radical in which the alkyl, aryl, aralkyl moiety has from about 2 to about 20 carbon atoms.

13. The composition of claim 12 comprising:
   a. about 5 wt. % to about 12 wt. % of a polyamide resin comprising a condensation product of a dicarboxylic acid and a diamine;
   b. about 13 wt. % to about 28 wt. % of liquid castor oil;
   c. about 35 wt. % to about 45 wt. % of isoeicosane;
   d. about 3 wt. % to about 7 wt. % of polybutene; and
   e. about 1 wt. % to about 10 wt. % of N-lauroyl-glutamic acid dibutylamide.

14. The composition of claim 12 essentially free of volatile alcohols.

15. The composition of claim 12 wherein said composition is translucent or transparent.

* * * * *